(12) United States Patent
Inoue

(10) Patent No.: US 10,459,214 B2
(45) Date of Patent: Oct. 29, 2019

(54) OBJECTIVE OPTICAL SYSTEM FOR ENDOSCOPE AND ENDOSCOPE

(71) Applicant: FUJIFILM Corporation, Tokyo (JP)

(72) Inventor: Kazuki Inoue, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 396 days.

(21) Appl. No.: 15/470,658

(22) Filed: Mar. 27, 2017

(65) Prior Publication Data

US 2017/0285322 A1 Oct. 5, 2017

(30) Foreign Application Priority Data

Apr. 4, 2016 (JP) ................. 2016-074867

(51) Int. Cl.
*G02B 23/24* (2006.01)
*A61B 1/00* (2006.01)
*G02B 7/105* (2006.01)
*G02B 9/60* (2006.01)
*G02B 13/04* (2006.01)

(52) U.S. Cl.
CPC ........ *G02B 23/243* (2013.01); *A61B 1/00096* (2013.01); *A61B 1/00163* (2013.01); *G02B 7/105* (2013.01); *G02B 9/60* (2013.01); *G02B 13/04* (2013.01); *G02B 23/2415* (2013.01)

(58) Field of Classification Search
CPC ............ A61B 1/00096; A61B 1/00163; G02B 23/243; G02B 23/2438; G02B 9/10; G02B 13/006; G02B 13/04; H04N 5/2254
See application file for complete search history.

(56) References Cited

U.S. PATENT DOCUMENTS

2011/0002052 A1* 1/2011 Nasu .................... G02B 15/177
359/717
2013/0137930 A1* 5/2013 Menabde ........... A61B 1/00096
600/168

(Continued)

FOREIGN PATENT DOCUMENTS

JP H07-218827 A 8/1995
JP H11-014902 A 1/1999

(Continued)

OTHER PUBLICATIONS

An Office Action mailed by the Japanese Patent Office dated Jun. 4, 2019, which corresponds to Japanese Patent Application No. 2016-074867 and is related to U.S. Appl. No. 15/470,658.

*Primary Examiner* — John P Leubecker
(74) *Attorney, Agent, or Firm* — Studebaker & Brackett PC

(57) ABSTRACT

An objective optical system for an endoscope consists of a front group, an aperture stop, and a positive rear group in order from an object side. The front group consists of a negative first lens having a smaller absolute value of a curvature radius of a lens surface on an image side than that on an object side, and one or more parallel planar members of which an incidence surface and an emission surface are perpendicular to an optical axis, in order from the object side. The rear group consists of a positive second lens and a cemented lens in which a negative third lens, and a positive fourth lens are joined together in order from the object side and a cemented surface has a concave surface toward the image side. A predetermined conditional expression is satisfied.

20 Claims, 6 Drawing Sheets

EXAMPLE 1

(56) References Cited

U.S. PATENT DOCUMENTS

| | | | |
|---|---|---|---|
| 2014/0307333 A1* | 10/2014 | Kawamura | G02B 13/0045 359/708 |
| 2015/0359422 A1* | 12/2015 | Igarashi | G02B 23/243 600/135 |
| 2016/0178885 A1* | 6/2016 | Harada | G02B 27/0025 359/753 |
| 2017/0038563 A1* | 2/2017 | Sato | G02B 13/04 |
| 2017/0224201 A1* | 8/2017 | Yamamoto | A61B 1/00163 |
| 2018/0231749 A1* | 8/2018 | Namii | G02B 13/04 |

FOREIGN PATENT DOCUMENTS

| | | |
|---|---|---|
| JP | 2002-277735 A | 9/2002 |
| JP | 3574484 B2 | 10/2004 |
| JP | 3851417 B2 | 11/2006 |
| JP | 4439184 B2 | 3/2010 |
| JP | 2015-034885 A | 2/2015 |

\* cited by examiner

EXAMPLE 1

EXAMPLE 2

EXAMPLE 3

OBJECTIVE OPTICAL SYSTEM FOR ENDOSCOPE AND ENDOSCOPE

CROSS REFERENCE TO RELATED APPLICATIONS

The present application claims priority under 35 U.S.C. § 119 to Japanese Patent Application No. 2016-074867 filed on Apr. 4, 2016. The above application is hereby expressly incorporated by reference, in its entirety, into the present application.

BACKGROUND OF THE INVENTION

1. Field of the Invention

The invention relates to an objective optical system for an endoscope and an endoscope including this objective optical system for an endoscope.

2. Description of the Related Art

In the related art, insertion-type endoscopes in which an elongated insertion part having an imaging device built in a distal portion is inserted through a mouth or nose of a subject, and the inside of a body cavity is imaged have been prevalent in the medical field. As objective optical systems that are available for such endoscopes, for example, there are those described in the following JP4439184B, JP3851417B, and JP3574484B. Lens systems including a lens group having negative refractive power, an aperture stop, and a lens group having positive refractive power, in order from an object side, is described in JP4439184B, JP3851417B, and JP3574484B.

SUMMARY OF THE INVENTION

In order to improve the detection rate of lesions, it is required for the objective optical systems for an endoscope to be wide-angle optical systems capable of observing a wide range. In the wide-angle optical systems, distortion becomes easily large. However, in recent years, images with little distortion even in an imaging region peripheral part have been required. However, since the objective optical systems for an endoscope described in JP4439184B JP3851417B, and JP3574484B have the large distortion, it is difficult to sufficiently meet the above requirements.

The invention has been made in view of the above circumstances, and an object thereof is to provide an objective optical system for an endoscope that is reduced in distortion while giving a wide angle and is capable of realizing excellent optical performance, and an endoscope including this objective optical system for an endoscope.

An objective optical system for an endoscope of the invention consists of a front group having negative refractive power as a whole, an aperture stop, and a rear group having positive refractive power as a whole, in order from an object side. The front group consists of a first lens, having negative refractive power, in which an absolute value of a curvature radius of a lens surface on an image side is smaller than an absolute value of a curvature radius of a lens surface on an object side, and at least one parallel planar member of which an incidence surface and an emission surface are perpendicular to an optical axis, in order from the object side. The rear group consists of a second lens having positive refractive power, a third lens having negative refractive power, and a fourth lens having positive refractive power, in order from the object side. The third lens and the fourth lens are joined together to constitute a cemented lens, and a cemented surface of the cemented lens has a concave surface directed to the image side. The following Conditional Expression (1) is satisfied.

$$0.02 < f/fc < 0.10 \quad (1)$$

where
f: Focal distance of entire system
fc: Focal distance of cemented lens

In objective optical system for an endoscope of the invention, it is preferable that at least one of the following Conditional Expressions (2) to (10) and (1-1) to (9-1) is satisfied.

$$0.51 < f/f2 < 0.75 \quad (2)$$

$$-0.83 < f/f1 < -0.61 \quad (3)$$

$$0.49 < f/fr < 0.74 \quad (4)$$

$$0.55 < \max|IH/LRi| < 0.90 \quad (5)$$

$$0.19 < \text{ave}|IH/LRi| < 0.32 \quad (6)$$

$$1.79 < \min Ndp < 1.98 \quad (7)$$

$$1.82 < \text{ave} Ndp < 1.98 \quad (8)$$

$$0.30 < f/Rc < 0.60 \quad (9)$$

$$0.10 < Nd3 - Nd4 < 0.15 \quad (10)$$

$$0.04 < f/fc < 0.08 \quad (1-1)$$

$$0.53 < f/f2 < 0.73 \quad (2-1)$$

$$-0.80 < f/f1 < -0.64 \quad (3-1)$$

$$0.53 < f/fr < 0.70 \quad (4-1)$$

$$0.60 < \max|IH/LRi| < 0.85 \quad (5-1)$$

$$0.20 < \text{ave}|IH/LRi| < 0.31 \quad (6-1)$$

$$1.81 < \min Ndp < 1.95 \quad (7-1)$$

$$1.84 < \text{ave} Ndp < 1.96 \quad (8-1)$$

$$0.33 < f/Rc < 0.57 \quad (9-1)$$

where
f: Focal distance of entire system
f2: Focal distance of second lens
f1: Focal distance of first lens
fr: Focal distance of rear group
IH: Maximum image height
LRi: Curvature radius of i-th lens surfaces from object side in case where i is an integer of 1 to 7
max|IH/LRi|: Maximum value of |IH/LRi| of entire system
ave|IH/LRi|: Average value of |IH/LRi| of entire system
minNdp: Minimum value of refractive index with respect to the d line of positive lens of entire system
aveNdp: Average value of refractive index with respect to the d line of positive lens of entire system
Rc: Curvature radius of cemented surface of cemented lens
Nd3: Refractive index of third lens with respect to the d line Nd4: Refractive index of fourth lens with respect to the d line fc: Focal distance of cemented lens An endoscope of the invention comprises the objective optical system for an endoscope of the invention.

In addition, the above "consists of" is also intended that lenses having no practical power, optical elements other than lenses, such as a stop and/or a cover glass, lens flanges, and/or lens barrels may be included in addition to those mentioned as constituent elements.

In addition, it is supposed that the signs of the refractive power of the above lens groups, the signs of the refractive power of the lenses, the shapes of the lens surfaces, and the curvature radii of the lens surfaces are considered in a paraxial region in cases where aspheric surfaces are included. Additionally, all the values of the above conditional expressions are based on the d line (wavelength of 587.6 nm).

According to the invention, in the lens system consisting of the negative front group, the aperture stop, and the positive rear group, in order from the object side, the configurations of the front group and the rear group are set suitably, and the predetermined conditional expressions are satisfied. Therefore, it is possible to provide the objective optical system for an endoscope that is reduced in distortion while giving a wide angle and is capable of realizing excellent optical performance, and the endoscope including this objective optical system for an endoscope.

DESCRIPTION OF THE PREFERRED EMBODIMENTS

Figure 1:
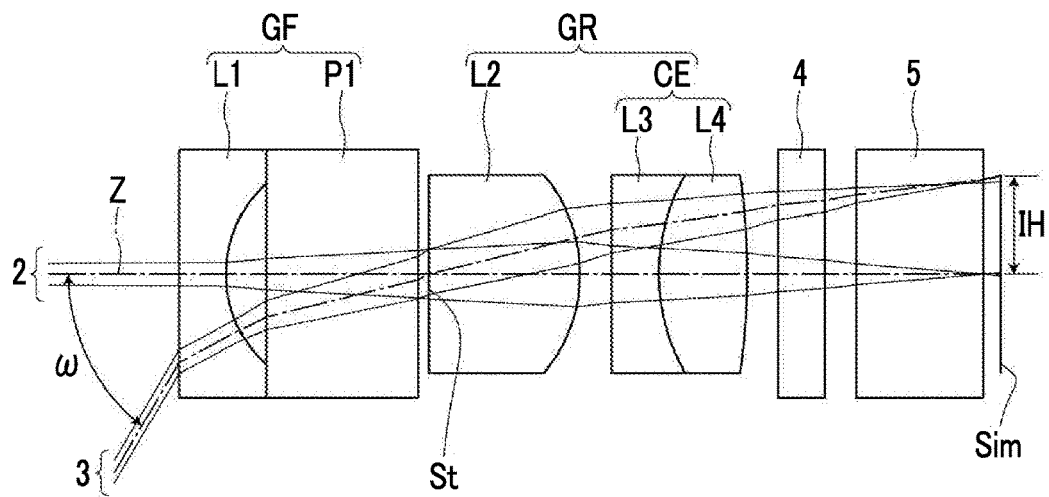
FIG. 1 is a sectional view illustrating the configuration and light paths of an objective optical system for an endoscope related to an embodiment of the invention, and is a sectional view corresponding to Example 1 of the invention.

Hereinafter, an embodiment of the invention will be described in detail with reference to the drawings. FIG. 1 is a sectional view illustrating the lens configuration and light paths of the objective optical system for an endoscope related to an embodiment of the invention. This configuration example corresponds to Example 1 to be described below. In FIG. 1, a left side is an object side, a right side is an image side, the light paths are illustrated regarding an on-axis light beam 2 and an off-axis light beam 3 of a maximum angle of view, and a maximum half angle of view (a half value of the maximum angle of view) to is also illustrated.

This objective optical system for an endoscope consists of a front group GF having negative refractive power as a whole, an aperture stop St, and a rear group GR having positive refractive power as a whole in order from the object side toward the image side along an optical axis Z. By arranging the negative lens group and the positive lens group in order from the object side in this way, a retro-focus type refractive power arrangement is obtained. Therefore, wider angle can be achieved while securing a back focus.

In addition, the aperture stop St illustrated in FIG. 1 does not necessarily indicate a size and/or a shape, and indicates a position on the optical axis Z. Additionally, FIG. 1 illustrates an example in which a filter 4 and a prism 5 are arranged between a lens system and an image plane Sim. However, a configuration in which the filter 4 and/or the prism 5 are omitted is also possible in the invention. Although the prism 5 may have a function of curving the light paths, and the light paths become curved light paths in that case, FIG. 1 illustrates linear light paths supposing a state where the light paths are deployed, in order to make the invention easily understood.

The front group GF is configured so as to consist of a first lens L1 having negative refractive power, and at least one parallel planar member P1 in which an incidence surface and an emission surface are perpendicular to the optical axis Z of the objective optical system for an endoscope, in order from the object side.

The first lens L1 is configured such that an absolute value of the curvature radius of a lens surface on the image side becomes smaller than an absolute value of the curvature radius of a lens surface on the object side. By adopting such a shape, it becomes easy to suppress image plane curving, and it becomes advantageous to achieve wider angle.

By adopting in which the objective optical system for an endoscope includes the parallel planar member P1 and the parallel planar member P1 is arranged closer to the object side than the aperture stop St, the height, from the optical axis Z, of a point where a light ray of a peripheral angle of view intersects the surface of the first lens L1 on the object side can be made low, and it becomes advantageous to reduce the diameter of the first lens L1. Since the parallel planar member P1 has no paraxial refractive power while having the above working, the influence that the parallel planar member has on optical performance is small compared with lenses in a case where the parallel planar member is eccentric. Specifically, even if the parallel planar member P1 is parallel-eccentric, deterioration of an image does not occur, and the allowable amount of a tilt error can be made large compared to lenses. For this reason, assembling becomes easy, which can contribute to realization of excellent optical performance. In addition, the "parallel eccentric" means movement in a direction perpendicular to the optical axis Z, and the "tilt" of the "tilt error" means rotation within a cross-section including the optical axis Z.

The parallel planar member P1 of FIG. 1 is constituted by parallel planar plates of which the incidence surface and the emission surface are parallel to each other. A configuration in which a filtering function is given to the parallel planar member P1 may be adopted if needed. In addition, the parallel planar member of the front group GF may be a prism. In a case where the parallel planar member is constituted by a prism and the optical axis is curved inside this prism, the incidence surface and the emission surface just have to be parallel to each other when the light paths are not curved but deployed linearly, without taking this curving inside the prism into consideration. However, it is preferable that the distribution of refractive index inside the parallel planar member is substantially uniform.

Although FIG. 1 illustrates an example in which the front group GF has only one parallel planar member P1, the number of parallel planar members of the front group GF can be selected arbitrarily. For example, in a case where there is a plurality of parallel planar members made of the same material, one parallel planar member having the same thickness as the total of the thicknesses of these parallel planar members and made of the same material, since the above plurality of parallel planar members exhibits the same effects in geometrical optics if surface reflection is ignored, the number and thicknesses of parallel planar members can be changed appropriately. Additionally, the front group GF may have a configuration in which the front group has a plurality of parallel planar members made of mutually different materials.

Since the first lens L1 is a negative lens in which the absolute value of the curvature radius of the lens surface on the image side becomes smaller than the absolute value of the curvature radius of the lens surface on the object side, the lens surface of the first lens L1 on the image side becomes a concave surface. It is preferable that a planar part perpendicular to the optical axis Z is provided closer to a radial outer side than this concave surface in the surface of the first lens L1 on the image side, and as illustrated in FIG. 1, this planar part and the parallel planar member P1 adjacent to the first lens L1 are configured so as to abut against each other in an optical axis direction. In such a case, the tilt of the first lens L1 can be prevented from occurring, and the performance deterioration caused by a manufacturing error can be reduced.

In a case where the planar part of the first lens L1 and the parallel planar member P1 are made to abut against each other as described above, if this planar part is provided circularly, a space formed by the concave surface of the first lens L1 on the image side and the surface of the parallel planar member P1 on the object side can be sealed without using other members, and can be kept airtight. Although the objective optical system for an endoscope is cooled, for example, by the supply of water for removing dirt adhering to the surface of the first lens L1 on the object side exposed to the outside, or the like, occurrence of dew condensation can be suppressed and permeation of humidity into this space can be suppressed, by making the above space airtight.

Additionally, in a case where the objective optical system for an endoscope is configured in a separable manner as will be described below in detail, various effects can be exhibited because the front group GF has at least one parallel planar member.

The rear group GR consists of a second lens L2 having positive refractive power, a third lens L3 having negative refractive power, and a fourth lens L4 having positive refractive power in order from the object side, and the third lens L3 and the fourth lens L4 are cemented together to constitute a cemented lens CE.

The spherical aberration can be suppressed by the second lens L2 having positive refractive power. The lateral chromatic aberration can be suppressed by the cemented lens CE. By arranging the cemented lens CE closest to the image side of the lens system, the height of a peripheral light ray in the cemented surface of the cemented lens CE can be made high, and excellent correction of the lateral chromatic aberration becomes easy.

Additionally, in this objective optical system for an endoscope, the cemented surface of the cemented lens CE is configured so as to have a shape in which the concave surface is directed to the image side. Accordingly, it becomes advantageous to suppress the lateral chromatic aberration.

The lens surface of the second lens L2 on the object side may have a planar surface. In such a case, since the allowable amount of the tilt error can be made large, the assembling becomes easy. Additionally, the lens surface of the third lens L3 on the object side may be a planar surface. In such a case, since the allowable amount of the tilt error can be made large, the assembling becomes easy.

Additionally, this objective optical system for an endoscope is configured so as to satisfy the following Conditional Expression (1).

$$0.02 < f/fc < 0.10 \tag{1}$$

where f: Focal distance of entire system fc: Focal distance of cemented lens

By bringing about a state where a lower limit or lower of Conditional Expression (1) is not established, the angle of incidence of a principal light ray of a peripheral angle of view to the image plane Sim can be suppressed, and it becomes advantageous to achieve wider angle. By bringing out a state where an upper limit or higher of Conditional Expression (1) is not established, the distortion can be suppressed. In order to further enhance effects regarding Conditional Expression (1), it is preferable to satisfy the following Conditional Expression (1-1).

$$0.04 < f/fc < 0.08 \tag{1-1}$$

Additionally, it is preferable that this objective optical system for an endoscope satisfies the following Conditional Expression (2).

$$0.51 < f/f2 < 0.75 \tag{2}$$

where f: Focal distance of entire system f2: Focal distance of second lens

By setting the range of the refractive power of the second lens L2 so as to satisfy Conditional Expression (2), the image plane curving can be suppressed. In order to further enhance effects regarding Conditional Expression (2), it is preferable to satisfy the following Conditional Expression (2-1).

$$0.53 < f/f2 < 0.73 \tag{2-1}$$

Additionally, it is preferable that this objective optical system for an endoscope satisfies the following Conditional Expression (3).

$$-0.83 < f/f1 < -0.61 \tag{3}$$

where f: Focal distance of entire system f1: Focal distance of first lens

By bringing out a state where a lower limit or lower of Conditional Expression (3) is not established, the image plane curving can be suppressed. By bringing out a state where an upper limit or higher of Conditional Expression (3) is not established, it becomes easy to maintain the angle of view while suppressing the diameter of a lens. In order to further enhance effects regarding Conditional Expression (3), it is preferable to satisfy the following Conditional Expression (3-1).

$$-0.80 < f/f < -0.64 \qquad (3\text{-}1)$$

Additionally, it is preferable that this objective optical system for an endoscope satisfies the following Conditional Expression (4).

$$0.49 < f/fr < 0.74 \qquad (4)$$

where
f: Focal distance of entire system
fr: Focal distance of rear group

By bringing about a state where a lower limit or lower of Conditional Expression (4) is not established, the angle of incidence of a principal light ray of a peripheral angle of view to the image plane Sim can be suppressed, and it becomes advantageous to achieve wider angle. By bringing out a state where an upper limit or higher of Conditional Expression (4) is not established, the distortion can be suppressed. In order to further enhance effects regarding Conditional Expression (4), it is preferable to satisfy the following Conditional Expression (4-1).

$$0.53 < f/fr < 0.70 \qquad (4\text{-}1)$$

Additionally, it is preferable that this objective optical system for an endoscope satisfies the following Conditional Expression (5).

$$0.55 < \max|IH/LRi| < 0.90 \qquad (5)$$

where
IH: Maximum image height
LRi: Curvature radius of i-th lens surfaces from object side in case where i is an integer of 1 to 7
max|IH/LRi|: Maximum value of |IH/LRi| of entire system In addition, the "lens surfaces" of the above "LRi" are a lens surface on the object side and a lens surface on the image side that each of four lenses of the first lens L1 to the fourth lens L4 has. Here, in the "lens surfaces" of "LRi", cemented surfaces are treated as one surface. Therefore, in the objective optical system for an endoscope of the present embodiment, the "lens surfaces" of "LRi" are seven in total. These points regarding the "lens surfaces" of "LRi" are the same also in "LRi" of Conditional Expression (6) to be described below.

By bringing out a state where a lower limit or lower of Conditional Expression (5) is not established, the image plane curving can be suppressed. By bringing about a state where an upper limit or higher of Conditional Expression (5) is not established, the allowable amount of the parallel eccentricity of a lens and the allowable amount of the tilt error can be made large, and the assembling becomes easy, which can contribute to realization of excellent optical performance. In order to further enhance effects regarding Conditional Expression (5), it is preferable to satisfy the following Conditional Expression (5-1).

$$0.60 < \max|IH/LRi| < 0.85 \qquad (5\text{-}1)$$

Additionally, it is preferable that this objective optical system for an endoscope satisfies the following Conditional Expression (6).

$$0.19 < ave|IH/LRi| < 0.32 \qquad (6)$$

where
IH: Maximum image height
LRi: Curvature radius of i-th lens surfaces from object side in case where i is an integer of 1 to 7
ave|IH/LRi|: Average value of |IH/LRi| of entire system By bringing out a state where a lower limit or lower of Conditional Expression (6) is not established, the image plane curving can be suppressed. By bringing about a state where an upper limit or higher of Conditional Expression (6) is not established, the allowable amount of the parallel eccentricity of a lens and the allowable amount of the tilt error can be made large, and the assembling becomes easy, which can contribute to realization of excellent optical performance. In order to further enhance effects regarding Conditional Expression (6), it is preferable to satisfy the following Conditional Expression (6-1).

$$0.20 < ave|IH/LRi| < 0.31 \qquad (6\text{-}1)$$

Additionally, it is preferable that this objective optical system for an endoscope satisfies the following Conditional Expression (7).

$$1.79 < minNdp < 1.98 \qquad (7)$$

where
minNdp: Minimum value of refractive index of positive lens of entire system with respect to the d line By bringing out a state where a lower limit or lower of Conditional Expression (7) is not established, the spherical aberration can be suppressed. By bringing out a state where an upper limit or higher of Conditional Expression (7) is not established, the image plane curving can be suppressed. In order to further enhance effects regarding Conditional Expression (7), it is preferable to satisfy the following Conditional Expression (7-1).

$$1.81 < minNdp < 1.95 \qquad (7\text{-}1)$$

Additionally, it is preferable that this objective optical system for an endoscope satisfies the following Conditional Expression (8).

$$1.82 < aveNdp < 1.98 \qquad (8)$$

where
aveNdp: Average value of refractive index of positive lens of entire system with respect to the d line By bringing out a state where a lower limit or lower of Conditional Expression (8) is not established, the spherical aberration can be suppressed. By bringing out a state where an upper limit or higher of Conditional Expression (8) is not established, the image plane curving can be suppressed. In order to further enhance effects regarding Conditional Expression (8), it is preferable to satisfy the following Conditional Expression (8-1).

$$1.84 < aveNdp < 1.96 \qquad (8\text{-}1)$$

Additionally, it is preferable that this objective optical system for an endoscope satisfies the following Conditional Expression (9).

$$0.30 < f/Rc < 0.60 \qquad (9)$$

where
f: Focal distance of entire system
Rc: Curvature radius of cemented surface of cemented lens By bringing out a state where a lower limit or lower of Conditional Expression (9) is not established, the spherical aberration can be suppressed. By bringing out a state where an upper limit or higher of Conditional Expression (9) is not established, the astigmatism can be suppressed. In order to further enhance effects regarding Conditional Expression (9), it is preferable to satisfy the following Conditional Expression (9-1).

$$0.33 < f/Rc < 0.57 \qquad (9\text{-}1)$$

Additionally, it is preferable that this objective optical system for an endoscope satisfies the following Conditional Expression (10).

$$0.10 < Nd3 - Nd4 < 0.15 \qquad (10)$$

where

Nd3: Refractive index of third lens with respect to the d line

Nd4: Refractive index of fourth lens with respect to the d line

By bringing out a state where a lower limit or lower of Conditional Expression (10) is not established, the spherical aberration can be suppressed. By bringing out a state where an upper limit or higher of Conditional Expression (10) is not established, the image plane curving can be suppressed. In order to further enhance effects regarding Conditional Expression (10), it is preferable to satisfy the following Conditional Expression (10-1).

$$0.11 < Nd3 - Nd4 < 0.14 \qquad (10\text{-}1)$$

In addition, this objective optical system for an endoscope may be configured such that the first lens L1 and the parallel planar member P1 are separable with respect to an optical member closer to the image side than the parallel planar member P1. That is, in the example of FIG. 1, the front group GF may configured so as to be separable with respect to the aperture stop St and the rear group GR. In that case, it is possible to adopt a configuration in which a lens barrel to which the front group GF is fixed and a lens barrel to which the aperture stop St and the rear group GR are fixed are constituted by separate members, and these two lens barrels are be bonded together with an adhesive capable of being discomposed due to an external stimulus, such as a solvent, heat, or light. By adopting such a separable configuration, it is possible to decompose and remove the above adhesive to integrally replace the lens barrel including the first lens L1 with another, in a case where soiling or damaging has occurred on the first lens L1.

The first lens L1 that is arranged closest to the object side and is exposed to the outside may be soiled and damaged with use. In a case where soiling or damaging has occurred on the first lens L1, replacement of the entire objective optical system for an endoscope should be performed if the objective optical system for an endoscope is integrally configured in a separable manner. As a result, repair cost increases. In contrast, in the objective optical system for an endoscope in which only some optical members on the object side is configured in a replaceable manner similar to the above configuration, costs regarding the replacement can be reduced.

In a case where the separable configuration as described above is adopted, since the front group GF has the parallel planar member P1, it is possible to seal the front group GF on the image side using the parallel planar member P1. Therefore, handling becomes easy at the time of separation. As a result, it becomes easy to remove and clean dust, dirt, or the like.

In addition, the front group GF may have a plurality of parallel planar members. In that case, it is preferable that the first lens L1, and a parallel planar member closest to the object side are configured to be separable with respect to a second parallel planar member from the object side, and an optical member closer to the image side than the second parallel planar member. Accordingly, it is possible to seal optical members on the image side after this second parallel planar member, with the second parallel planar member from the object side. Therefore, similarly, at the time of separation, handling becomes easy, and maintenance becomes easy.

It is preferable that the preferable configurations and allowable configurations that are described above are possible by arbitrary combinations, and are appropriately selectively adopted according to required specifications. According to the present embodiment, an objective optical system for an endoscope in which various aberrations including the distortion are suppressed while giving a wide angle, and excellent optical performance is given, can be realized. In addition, the wide angle herein means that the full maximum angle of view is 100° or more.

Next, numerical examples of the objective optical system for an endoscope of the invention will be described.

Example 1

The lens configuration and light paths of an objective optical system for an endoscope of Example 1 are illustrated in FIG. 1, and since an illustration method thereof is as described above, the duplicate description thereof will be omitted herein. The basic lens data of the objective optical system for an endoscope of Example 1 are illustrated in Table 1. i-th surface numbers (i=1, 2, 3, . . . ) in a case where surface numbers are given to surfaces of constituent elements so as to increase sequentially toward the image side with an object-side surface of a constituent element closest to the object side being a first constituent element are shown in a column Si of Table 1, the curvature radii of i-th surfaces are shown in a column Ri, and the surface intervals on the optical axis Z between i-th surfaces and i+1-th surfaces are shown in a column Di. Refractive indexes of constituent elements, which increase sequentially toward the image side with an object-side surface of a constituent element closest to the object side being a first constituent element, with respect to the d line (wavelength of 587.6 nm) of j-th (j=1, 2, 3, . . . ) are shown in a column Ndj of Table 1, and d line-based Abbe numbers of the j-th constituent elements are shown in a column vdj.

As for the signs of the curvature radii, the sign of the curvature radius of a surface shape in which a convex surface is directed to the object side is positive, and the sign of the curvature radius of a surface shape in which the convex surface is directed to the image side is negative. The aperture stop St, the filter 4, and the prism 5 are also shown together in Table 1. In Table 1, words, such as surface number and (St), are described in a column of the surface numbers of surfaces equivalent to the aperture stop St. The value at the lowest of the column Di is the spacing between the surface closest to the image side and the image plane Sim.

A focal distance f of the entire system, an F number FNo., a maximum angle 2ω of view, an object distance (a distance on the optical axis from the lens surface of the first lens L1 on the object side to an object) OB, and a maximum image height IH are shown on the basis of a d line at an upper part outside the frame of Table 1. The value at the lowest of the column Di of Table 1, and aberration diagrams to be described below are those in a case where the object distance is a value illustrated in Table 1.

In the data of respective tables, the degree is used for the unit of the angle, and mm is used for the unit of length. However, since an optical system can be used even if the optical system is proportionally magnified or proportionally diminished, other suitable units can be used. Additionally, numerical values rounded off at a predetermined digit are described in the respective tables shown below.

TABLE 1

Example 1
f = 0.32, FNo. = 4.25, 2ω = 117.2, OB = 4, IH = 0.295

| Si | Ri | Di | Ndj | υdj |
|---|---|---|---|---|
| 1 | ∞ | 0.1500 | 1.88299 | 40.78 |
| 2 | 0.3600 | 0.1255 | | |
| 3 | ∞ | 0.4800 | 1.91082 | 35.25 |
| 4 | ∞ | 0.0350 | | |
| 5(St) | ∞ | 0.0000 | | |
| 6 | ∞ | 0.4800 | 1.90043 | 37.37 |
| 7 | −0.4500 | 0.1000 | | |
| 8 | ∞ | 0.1500 | 1.95906 | 17.47 |
| 9 | 0.5800 | 0.2800 | 1.83481 | 42.72 |
| 10 | −1.9950 | 0.1000 | | |
| 11 | ∞ | 0.1500 | 1.85150 | 40.78 |
| 12 | ∞ | 0.1000 | | |
| 13 | ∞ | 0.4000 | 1.51633 | 64.14 |
| 14 | ∞ | 0.0535 | | |

Figure 4:
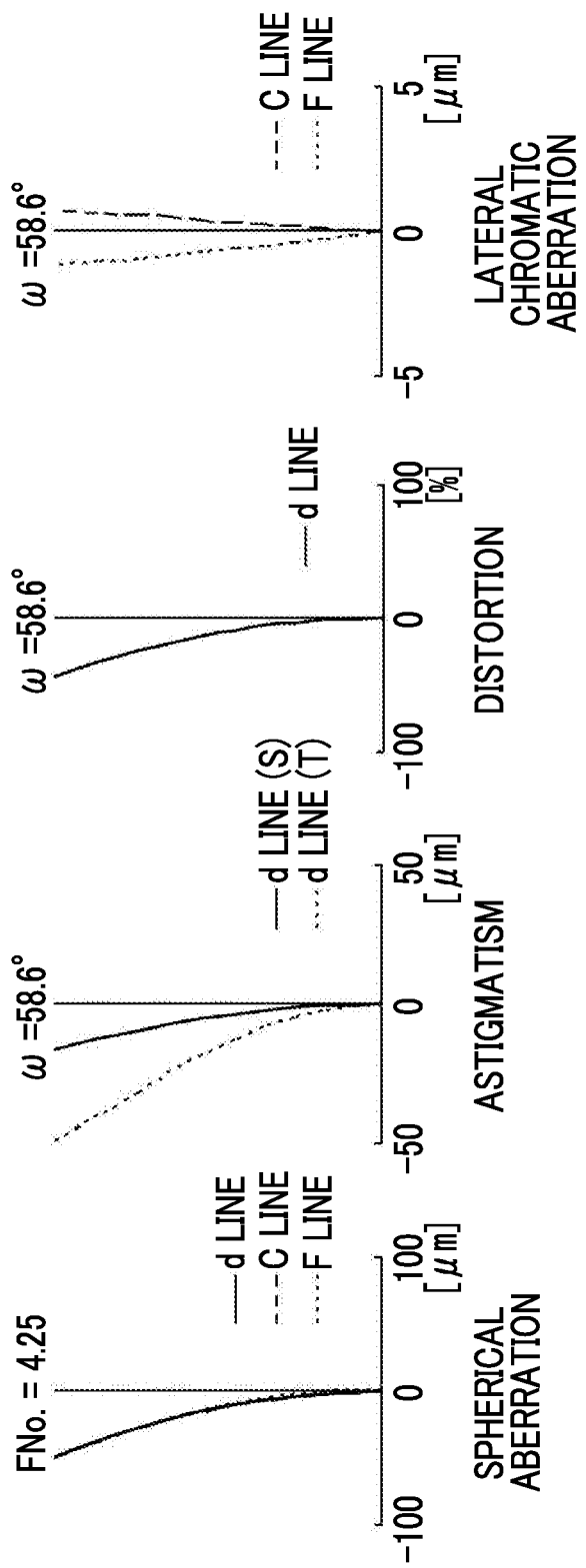
FIG. 4 is respective aberration diagrams of the objective optical system for an endoscope of Example 1 of the invention, and illustrates spherical aberration, astigmatism, distortion, and lateral chromatic aberration sequentially from the left.

Respective aberration diagrams of the spherical aberration, the astigmatism, the distortion, and the lateral chromatic aberration (lateral chromatic aberration) of the objective optical system for an endoscope of Example 1 of the invention are illustrated sequentially from the left in FIG. 4. In a spherical aberration diagram, aberrations regarding the d line (wavelength of 587.6 nm), the C line (wavelength of 656.3 nm), and the F line (wavelength of 486.1 nm), are respectively illustrated a solid line, a long dashed line, and a short dashed line. In an astigmatism diagram, an aberration regarding the d line in a sagittal direction is illustrated by a solid line, and an aberration regarding of the d line in a tangential direction is illustrated by a short dashed line. In a distortion diagram, an aberration regarding the d line is illustrated by a solid line. In a lateral chromatic aberration diagram, aberrations regarding the C line and the F line are respectively illustrated by a long dashed line and a short dashed line. FNo. of the spherical aberration diagram means the F number, and ω of the other aberration diagrams means a half angle of view.

Since the illustration method and the symbols, meanings, and description method of each data, which are described in the description regarding the configuration example of the above Example 1, are also the same in the following examples as long as they are not mentioned particularly, duplicate description will be omitted in the following.

Example 2

Figure 2:
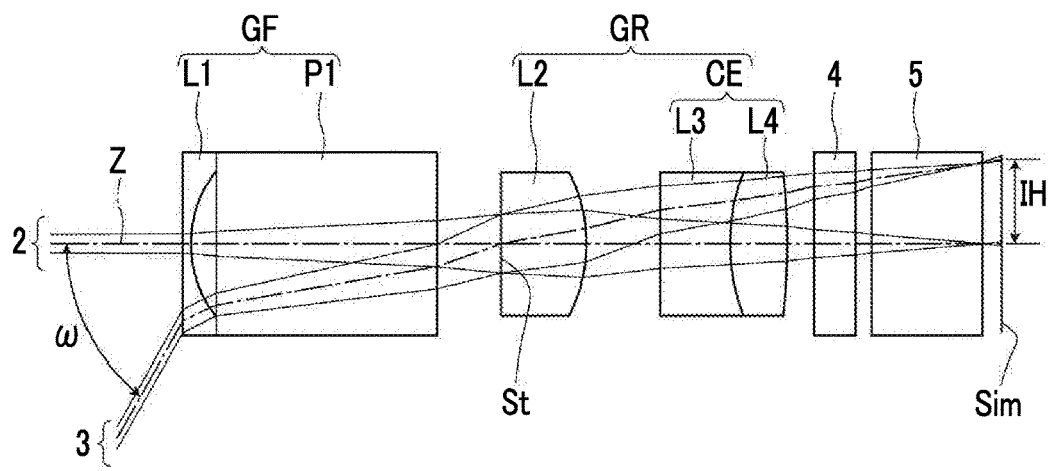
FIG. 2 is a sectional view illustrating the configuration and light paths of an objective optical system for an endoscope of Example 2 of the invention.
Figure 5:
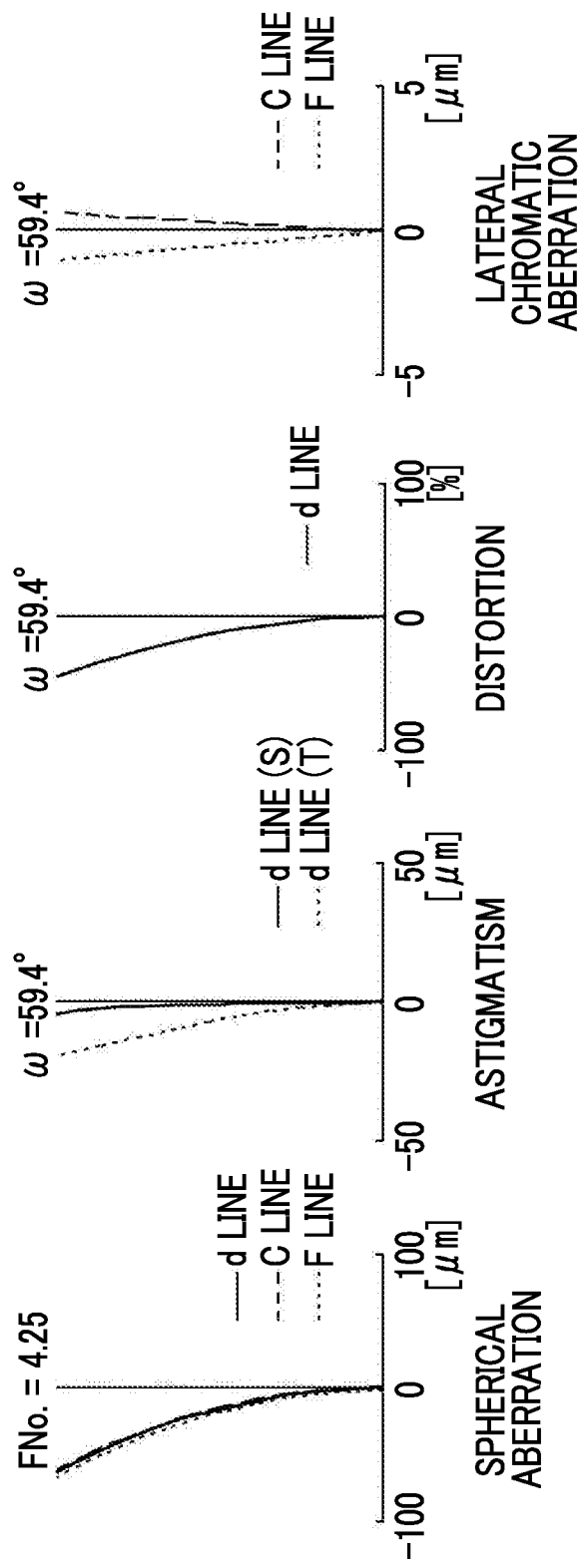
FIG. 5 is respective aberration diagrams of the objective optical system for an endoscope of Example 2 of the invention, and illustrates the spherical aberration, the astigmatism, the distortion, and the lateral chromatic aberration sequentially from the left.

With respect to an objective optical system for an endoscope of Example 2, lens configuration views and light paths are illustrated in FIG. 2, basic lens data are shown in Table 2, and respective aberration diagrams are illustrated in FIG. 5.

TABLE 2

Example 2
f = 0.32, FNo. = 4.25, 2ω = 118.8, OB = 4, IH = 0.295

| Si | Ri | Di | Ndj | υdj |
|---|---|---|---|---|
| 1 | ∞ | 0.0300 | 1.95375 | 32.32 |
| 2 | 0.4000 | 0.0930 | | |
| 3 | ∞ | 0.8000 | 1.94595 | 17.98 |
| 4 | ∞ | 0.2320 | | |

TABLE 2-continued

Example 2
f = 0.32, FNo. = 4.25, 2ω = 118.8, OB = 4, IH = 0.295

| Si | Ri | Di | Ndj | υdj |
|---|---|---|---|---|
| 5(St) | ∞ | 0.0000 | | |
| 6 | ∞ | 0.3113 | 1.88100 | 40.14 |
| 7 | −0.5263 | 0.2670 | | |
| 8 | ∞ | 0.2507 | 1.94595 | 17.98 |
| 9 | 0.6667 | 0.2100 | 1.81600 | 46.57 |
| 10 | −2.2675 | 0.1000 | | |
| 11 | ∞ | 0.1500 | 1.85150 | 40.78 |
| 12 | ∞ | 0.0600 | | |
| 13 | ∞ | 0.4000 | 1.51633 | 64.14 |
| 14 | ∞ | 0.0711 | | |

Example 3

Figure 3:
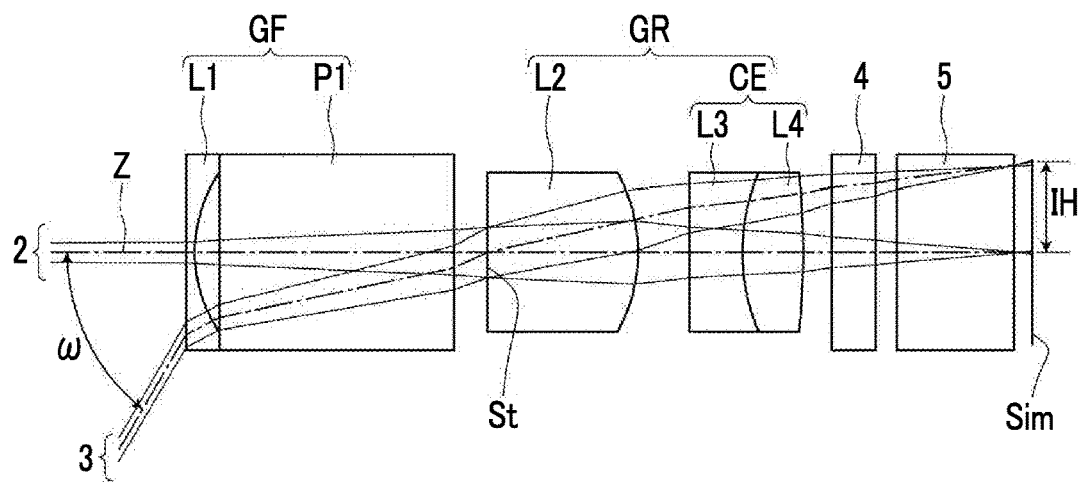
FIG. 3 is a sectional view illustrating the configuration and light paths of an objective optical system for an endoscope of Example 3 of the invention.
Figure 6:
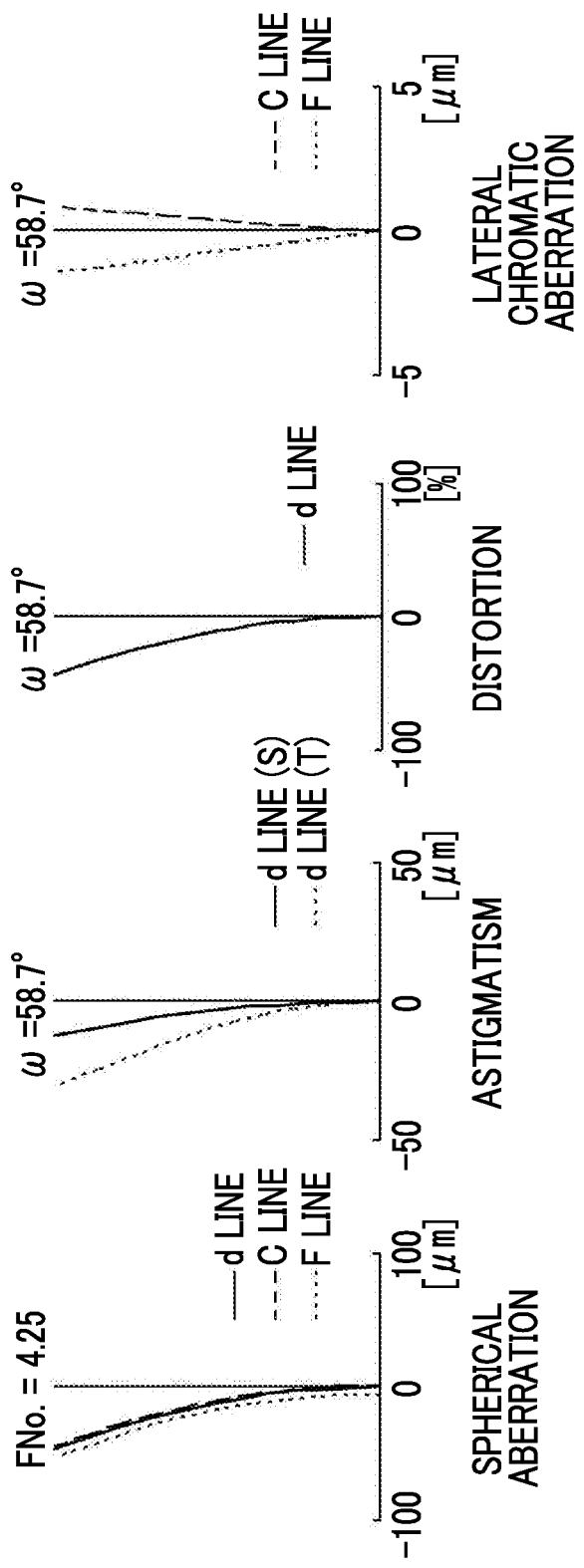
FIG. 6 is respective aberration diagrams of the objective optical system for an endoscope of Example 3 of the invention, and illustrates the spherical aberration, the astigmatism, the distortion, and the lateral chromatic aberration sequentially from the left.

With respect to an objective optical system for an endoscope of Example 3, lens configuration views and light paths are illustrated in FIG. 3, basic lens data are shown in Table 3, and respective aberration diagrams are illustrated in FIG. 6.

TABLE 3

Example 3
f = 0.32, FNo. = 4.25, 2ω = 117.4, OB = 4, IH = 0.295

| Si | Ri | Di | Ndj | υdj |
|---|---|---|---|---|
| 1 | ∞ | 0.0300 | 1.90043 | 37.37 |
| 2 | 0.4444 | 0.0845 | | |
| 3 | ∞ | 0.8000 | 2.00178 | 19.32 |
| 4 | ∞ | 0.1145 | | |
| 5(St) | ∞ | 0.0000 | | |
| 6 | ∞ | 0.5164 | 1.91082 | 35.25 |
| 7 | −0.5128 | 0.1759 | | |
| 8 | ∞ | 0.1800 | 2.00178 | 19.32 |
| 9 | 0.6329 | 0.2100 | 1.88300 | 40.76 |
| 10 | −2.5000 | 0.1000 | | |
| 11 | ∞ | 0.1500 | 1.85150 | 40.78 |
| 12 | ∞ | 0.0700 | | |
| 13 | ∞ | 0.4000 | 1.51633 | 64.14 |
| 14 | ∞ | 0.0619 | | |

The correspondence values of Conditional Expressions (1) to (10) of the objective optical system for an endoscope of Examples 1 to 3 are shown in Table 4. The data of Table 4 are based on the d line.

TABLE 4

| Expression No. | | Example 1 | Example 2 | Example 3 |
|---|---|---|---|---|
| (1) | f/fc | 0.070 | 0.056 | 0.056 |
| (2) | f/f2 | 0.647 | 0.537 | 0.571 |
| (3) | f/f1 | −0.793 | −0.765 | −0.652 |
| (4) | f/fr | 0.651 | 0.534 | 0.578 |
| (5) | Max|IH/LRi| | 0.819 | 0.738 | 0.664 |
| (6) | ave|IH/LRi| | 0.304 | 0.267 | 0.260 |
| (7) | minNdp | 1.83481 | 1.81600 | 1.88300 |
| (8) | aveNdp | 1.86762 | 1.84850 | 1.89691 |
| (9) | f/Rc | 0.557 | 0.481 | 0.508 |
| (10) | Nd3 − Nd4 | 0.12425 | 0.12995 | 0.11878 |

As can be seen from the above data, in the objective optical systems for an endoscope of Examples 1 to 3, high optical performance is achieved by the various aberrations including the distortion being excellently corrected while realizing lens systems in which all the angles of view are wide angles with 117° or more.

Figure 7:
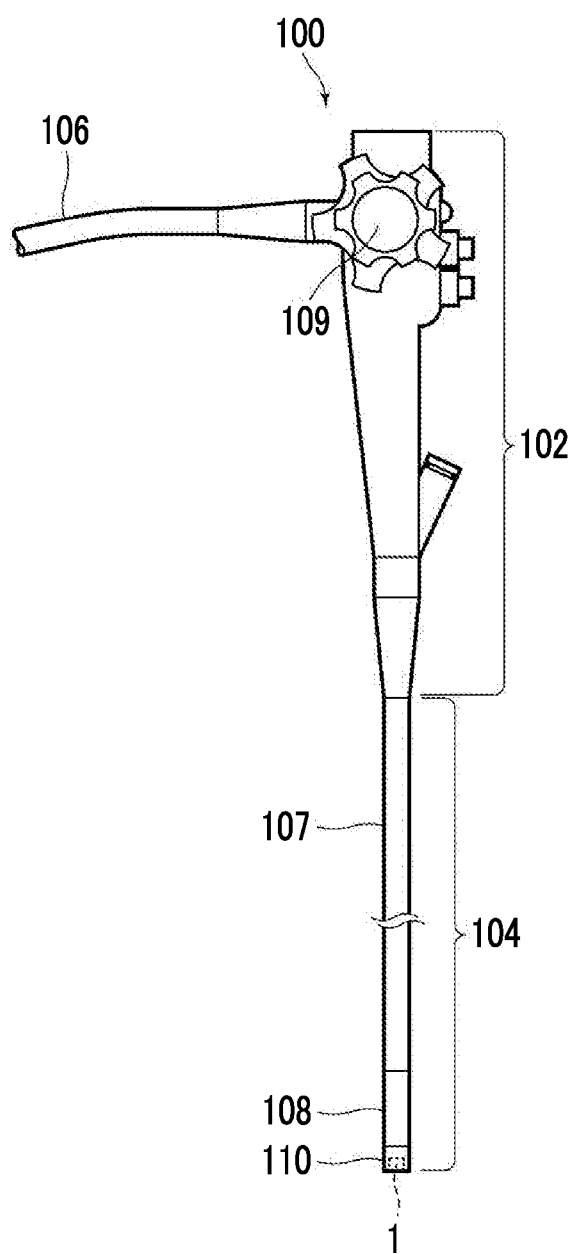
FIG. 7 is a view illustrating a schematic configuration of an endoscope related to the embodiment of the invention.

Next, an embodiment of the endoscope to which the objective optical system for an endoscope of the invention is applied will be described while referring to FIG. 7. A schematic overall configuration view of an endoscope is illustrated in FIG. 7. An endoscope 100 illustrated in FIG. 7 mainly includes an operating part 102, an insertion part 104, and a universal cord 106 connected to a connector part (not illustrated). Most of an insertion part 104 is a flexible part 107 that bends in arbitrary directions along an insertion path, a bending part 108 is coupled to the distal end of this flexible part 107, and a distal end part 110 is coupled to the distal end of the bending part 108. The bending part 108 is provided in order to direct the distal end part 110 in a desired direction, and a bending operation is possible by rotating a bending operation knob 109 provided in the operating part 102. The objective optical system 1 for an endoscope related to the embodiment of the invention is disposed at the distal end of the inside of the distal end part 110. In FIG. 7, the objective optical system 1 for an endoscope is illustrated schematically. Since the endoscope of the present embodiment includes the objective optical system 1 for an endoscope, excellent wide-angle images with little distortion even an imaging region peripheral part can be acquired.

Although the invention has been described above taking the embodiments and the examples, the invention is not limited to the above embodiments and examples, and various changes are possible. For example, the curvature radii, surface intervals, refractive indexes, and Abbe numbers of the respective lenses are not limited to the values shown in the above embodiments, and can take other values. Similarly, the number, thickness, and refractive indexes of the parallel planar plates of the front group GF are also not limited to the values illustrated in the above examples, either, and can take other values.

EXPLANATION OF REFERENCES

1: objective optical system for an endoscope
2: on-axis light beam
3: off-axis light beam
4: filter
5: prism
100: endoscope
102: operating part
104: insertion part
106: universal cord
107: flexible part
108: bending part
109: bending operation knob
110: distal end part
CE: cemented lens
GF: front group
GR: rear group
IH: maximum image height
L1: first lens
L2: second lens
L3: third lens
L4: fourth lens
P1: parallel planar member
Sim: image plane
St: aperture stop
Z: optical axis
ω: half angle of view

What is claimed is:

1. An objective optical system for an endoscope consisting of:
    a front group having negative refractive power as a whole, an aperture stop, and a rear group having positive refractive power as a whole, in order from an object side,
    wherein the front group consists of a first lens, having negative refractive power, in which an absolute value of a curvature radius of a lens surface on an image side is smaller than an absolute value of a curvature radius of a lens surface on an object side, and at least one parallel planar member of which an incidence surface and an emission surface are perpendicular to an optical axis, in order from the object side,
    wherein the rear group consists of a second lens having positive refractive power, a third lens having negative refractive power, and a fourth lens having positive refractive power, in order from the object side,
    wherein the third lens and the fourth lens are joined together to constitute a cemented lens, and a cemented surface of the cemented lens has a concave surface directed to the image side, and
    wherein the following Conditional Expression (1) is satisfied, $$0.02 < f/fc < 0.10 \tag{1}$$

where
f: Focal distance of entire system, and
fc: Focal distance of the cemented lens.

2. The objective optical system for an endoscope according to claim 1,
    wherein the following Conditional Expression (2) is satisfied, $$0.51 < f/f2 < 0.75 \tag{2}$$

where
f2: Focal distance of the second lens.

3. The objective optical system for an endoscope according to claim 2,
    wherein the following Conditional Expression (2-1) is satisfied, $$0.53 < f/f2 < 0.73 \tag{2-1}$$

4. The objective optical system for an endoscope according to claim 1,
    wherein the following Conditional Expression (3) is satisfied, $$-0.83 < f/f1 < -0.61 \tag{3}$$

where
f1: Focal distance of the first lens.

5. The objective optical system for an endoscope according to claim 4,
    wherein the following Conditional Expression (3-1) is satisfied, $$-0.80 < f/f1 < -0.64 \tag{3-1}$$

6. The objective optical system for an endoscope according to claim 1,
    wherein the following Conditional Expression (4) is satisfied, $$0.49 < f/fr < 0.74 \tag{4}$$

where
fr: Focal distance of the rear group.

7. The objective optical system for an endoscope according to claim 6, wherein the following Conditional Expression (4-1) is satisfied, $$0.53 < f/fr < 0.70 \tag{4-1}$$

8. The objective optical system for an endoscope according to claim 1,
wherein the following Conditional Expression (5) is satisfied, $$0.55 < \max|IH/LRi| < 0.90 \tag{5}$$

where
IH: Maximum image height,
LRi: Curvature radius of i-th lens surfaces from object side in case where i is an integer of 1 to 7, and
max|IH/LRi|: Maximum value of |IH/LRi| of entire system.

9. The objective optical system for an endoscope according to claim 8,
wherein the following Conditional Expression (5-1) is satisfied, $$0.60 < \max|IH/LRi| < 0.85 \tag{5-1}$$

10. The objective optical system for an endoscope according to claim 1,
wherein the following Conditional Expression (6) is satisfied, $$0.19 < ave|IH/LRi| < 0.32 \tag{6}$$

where
IH: Maximum image height,
LRi: Curvature radius of i-th lens surfaces from object side in case where i is an integer of 1 to 7, and
ave|IH/LRi|: Average value of |IH/LRi| of entire system.

11. The objective optical system for an endoscope according to claim 10,
wherein the following Conditional Expression (6-1) is satisfied, $$0.20 < ave|IH/LRi| < 0.31 \tag{6-1}$$

12. The objective optical system for an endoscope according to claim 1,
wherein the following Conditional Expression (7) is satisfied, $$1.79 < minNdp < 1.98 \tag{7}$$

where
minNdp: Minimum value of refractive index with respect to the d line of all positive lenses included in the entire system.

13. The objective optical system for an endoscope according to claim 12, wherein the following Conditional Expression (7-1) is satisfied, $$1.81 < minNdp < 1.95 \tag{7-1}$$

14. The objective optical system for an endoscope according to claim 1,
wherein the following Conditional Expression (8) is satisfied, $$1.82 < aveNdp < 1.98 \tag{8}$$

where
aveNdp: Average value of refractive index with respect to the d line of all positive lenses included in the entire system.

15. The objective optical system for an endoscope according to claim 14,
wherein the following Conditional Expression (8-1) is satisfied, $$1.84 < aveNdp < 1.96 \tag{8-1}$$

16. The objective optical system for an endoscope according to claim 1,
wherein the following Conditional Expression (9) is satisfied, $$0.30 < f/Rc < 0.60 \tag{9}$$

where
Rc: Curvature radius of cemented surface of the cemented lens.

17. The objective optical system for an endoscope according to claim 16,
wherein the following Conditional Expression (9-1) is satisfied, $$0.33 < f/Rc < 0.57 \tag{9-1}$$

18. The objective optical system for an endoscope according to claim 1,
wherein the following Conditional Expression (10) is satisfied, $$0.10 < Nd3 - Nd4 < 0.15 \tag{10}$$

where
Nd3: Refractive index of the third lens with respect to the d line, and
Nd4: Refractive index of the fourth lens with respect to the d line.

19. The objective optical system for an endoscope according to claim 1,
wherein the following Conditional Expression (1-1) is satisfied, $$0.04 < f/fc < 0.08 \tag{1-1}$$

20. An endoscope comprising:
the objective optical system for an endoscope according to claim 1.

* * * * *